(12) United States Patent
Thorsen et al.

(10) Patent No.: US 11,311,623 B2
(45) Date of Patent: Apr. 26, 2022

(54) NICOTINE DELIVERY PRODUCT, RELATED USES AND ORAL DOSAGE FORMS, AND METHODS OF PRODUCTION

(71) Applicant: Fertin Pharma A/S, Vejle (DK)

(72) Inventors: Jesper Thorsen, Klovborg (DK); Bjarne Vestbö, Fredericia (DK); Birgitte Kringelum Breindal, Kolding (DK); Jesper Neergaard, Aabenraa (DK)

(73) Assignee: Fertin Pharma A/S, Vejle (DK)

( * ) Notice: Subject to any disclaimer, the term of this patent is extended or adjusted under 35 U.S.C. 154(b) by 0 days.

(21) Appl. No.: 16/095,145

(22) PCT Filed: Apr. 21, 2016

(86) PCT No.: PCT/EP2016/058925
§ 371 (c)(1),
(2) Date: Oct. 19, 2018

(87) PCT Pub. No.: WO2017/182084
PCT Pub. Date: Oct. 26, 2017

(65) Prior Publication Data
US 2019/0134207 A1  May 9, 2019

(51) Int. Cl.
*A61K 9/14* (2006.01)
*A61K 47/58* (2017.01)
*A61K 9/00* (2006.01)
*A61K 9/68* (2006.01)
*A61K 31/465* (2006.01)
*A61K 9/16* (2006.01)

(52) U.S. Cl.
CPC .......... *A61K 47/585* (2017.08); *A61K 9/0053* (2013.01); *A61K 9/0056* (2013.01); *A61K 9/0058* (2013.01); *A61K 9/1617* (2013.01); *A61K 9/1635* (2013.01); *A61K 31/465* (2013.01)

(58) Field of Classification Search
None
See application file for complete search history.

(56) References Cited

U.S. PATENT DOCUMENTS

| | | | |
|---|---|---|---|
| 3,901,248 A | 8/1975 | Lichtneckert et al. | |
| 3,957,698 A | 5/1976 | Hatch | |
| 6,586,449 B1 | 7/2003 | Walling | |
| 6,828,336 B2 | 12/2004 | Walling | |
| 8,728,443 B2 | 5/2014 | Andersen | |
| 8,728,444 B2 | 5/2014 | Andersen | |
| 8,741,935 B2 | 6/2014 | Andersen | |
| 8,986,668 B2 | 3/2015 | Andersen | |
| 2004/0194793 A1 | 10/2004 | Lindell et al. | |
| 2008/0286340 A1 | 11/2008 | Andersson et al. | |
| 2009/0092573 A1 | 4/2009 | Andersen | |
| 2010/0130562 A1 | 5/2010 | Hite et al. | |
| 2010/0247586 A1 | 9/2010 | Hugerth et al. | |
| 2011/0165253 A1 | 7/2011 | Roehrich | |
| 2011/0214681 A1* | 9/2011 | Axelsson | A61K 9/009 131/369 |
| 2013/0071338 A1 | 3/2013 | Andersen | |
| 2013/0136797 A1 | 5/2013 | Mehta et al. | |
| 2013/0251779 A1* | 9/2013 | Svandal | A61K 31/465 424/440 |
| 2014/0230833 A1 | 8/2014 | Andersen | |

FOREIGN PATENT DOCUMENTS

| | | |
|---|---|---|
| CA | 2775323 A1 | 3/2011 |
| EP | 1190721 A2 | 3/2002 |
| WO | WO0025598 A1 | 5/2000 |
| WO | WO2004068965 A1 | 8/2004 |
| WO | WO2009080022 A1 | 7/2009 |
| WO | WO2009134947 A1 | 11/2009 |
| WO | WO2009141321 A2 | 11/2009 |

OTHER PUBLICATIONS

Conaghey et al., "The release of nictoine from a hydrogel containing ion exchange resins," Apr. 1998, International Journal of Pharmaceutics, 170:215-224.

International Search Report and Written Opinion dated Feb. 28, 2017 in International Application No. PCT/EP2016/058925, 13 pages.

Srikanth et al., "Ion-exchange resins as controlled drug delivery carriers," Aug. 2010, J. Sci. Res. 2(3): 597-611.

"Bio-Rex 70 Cation Exchange Resin, biotechnology grade, 50-100 mesh, sodium form 100 g #1435832" retrieved Apr. 21, 2021 from Bio-Rad Lab general product information, from https://www.bio-rad.com/de-de/sku/143 5832-bio-rex-70-cation-exchange-resin-biotec, 2 pages.

Bio-Rex Weakly Acidic Cation Exchange Resin Instruction Manual. Retrieved May 17, 2021 Bio-Rad Laboratories, Hercules, CA. LIT-206 Rev B, 11 pages.

"DOWEX Fine Mesh Shperical Ion Exchange Resins For Fine Chemical and Pharmaceutical Column Separations" Retrieved May 17, 2021 from Dow Water Solutions. 8 pages.

Notice of Opposition from European patent office for Application No. 16717648 mailed on May 2, 2021, a counterpart foreign application of U.S. Appl. No. 16/095,145, 7 pages.

* cited by examiner

*Primary Examiner* — Jessica Worsham
(74) *Attorney, Agent, or Firm* — Lee & Hayes, P.C.

(57) ABSTRACT

The present invention relates to a nicotine delivery product comprising, or even consisting essentially of, a population of nicotine-loaded cation exchange resin particles, said population comprises at least 50% (w/w) particles having a size in the range of 90-300 micron which provides an improved nicotine stability to oral dosage forms comprising the nicotine delivery product. The invention furthermore relates to methods of producing the nicotine delivery product and the oral dosage forms and to the use of the nicotine delivery product.

22 Claims, 1 Drawing Sheet

NICOTINE DELIVERY PRODUCT, RELATED USES AND ORAL DOSAGE FORMS, AND METHODS OF PRODUCTION

CROSS REFERENCE TO RELATED APPLICATIONS

This application is a U.S. National Phase Application of International Application No. PCT/EP2016/058925, filed Apr. 21, 2016, which is hereby incorporated by reference in its entirety.

FIELD OF THE INVENTION

The present invention relates to a nicotine delivery product comprising, or even consisting essentially of, a population of nicotine-loaded cation exchange resin particles, said population comprises at least 50% (w/w) particles having a size in the range of 90-300 micron, which provides an improved nicotine stability in oral dosage forms comprising the nicotine delivery product. The invention furthermore relates to methods of producing the nicotine delivery product and the oral dosage forms, and to the use of the nicotine delivery product.

BACKGROUND OF THE INVENTION

Nicotine is a well-known, highly characterized alkaloid that can be isolated from the dried leaves of Nicotiana tabacum. Its numerous commercial uses include utilities such as a fumigant, an insecticide and the like. It is furthermore therapeutically valuable in the treatment of the smoking withdrawal syndrome, for example in Nicotine Replacement Therapy. This treatment is based on the fact that the administration of nicotine into the body has been readily accomplished by smoking, e.g. from cigarettes, pipes or cigars. The smoker experiences a satisfactory sensation from such administration. However, smoking may be associated with health hazards not necessarily associated with administration of nicotine itself.

As a result, non-smoking methods have been devised to administer nicotine to the body. These include nicotine containing chewing gums, nicotine-impregnated dermal patches, nicotine inhalers and the like. A variety of patents have disclosed such products.

U.S. Pat. No. 3,901,248 discloses a chewable smoking substitute composition which comprises a chewing gum base and a nicotine/cation exchange resin complex dispersed in said gum base. When such composition is chewed, nicotine is released in small and reduced amounts into the mouth within the first few minutes of chewing. The composition is marginally effective in inducing the pleasurable sensation of smoking that is typically desired from those engaged in the therapy that incorporates such chewing gum.

U.S. Pat. No. 6,586,449 discloses a method for preparing a nicotine composition having a nicotine release rate of not less than 70% over a 10 minute period. The method comprises (a) mixing an aqueous solution of an organic polyol with a cation exchange resin selected from the group consisting of (i) a methacrylic, weakly acidic type of resin containing carboxylic functional groups, (ii) a polystyrene, strongly acidic type of resin containing sulfonic functional groups, and (iii) a polystyrene, intermediate acidic type of resin containing phosphonic functional groups, thereby forming a cation exchange resin mixture having some of its ion exchange sites partially blocked with said polyol; (b) admixing with said mixture of step (a) an aqueous solution of nicotine to form a nicotine-coated cation exchange resin admixture; and (c) removing water from said admixture to produce said nicotine composition having a nicotine release rate of not less than 70% over a 10 minute period.

U.S. Pat. No. 8,728,444 B2 discloses a method of producing a nicotine delivery product which method includes preparing a first mixture including nicotine, a cation exchange resin and water by mixing the constituent components of the first mixture. The method optionally includes removing up to 85 wt. % of the water contained in the first mixture to form a second mixture. A mixture selected from the first and second mixtures is then combined with further components to produce the nicotine delivery product.

U.S. Pat. No. 8,986,668 B2 discloses e.g. a method for preparing a nicotine delivery product, said method comprising (a) mixing nicotine, a cation exchange resin, an organic polyol and water to form a mixture wherein the total amount of water is from 26 to 45% by weight of the total mixture, and (b) removing water from the mixture to produce said nicotine delivery product. The nicotine delivery product obtained from this process is furthermore disclosed.

US 2014/0230833 discloses a nicotine delivery product comprising the reaction product of a nicotine/cation exchange resin complex and an organic polyol; and a method for preparing it comprising (a) mixing an aqueous suspension of a nicotine/cation exchange resin complex with an organic polyol or an aqueous solution thereof, and (b) removing water from the mixture to produce said nicotine delivery product. The nicotine delivery product has a nicotine release rate of at least 80% over a 10 minute period. It is particularly suited for use in smoking substitution devices delivering nicotine such as chewing gum, patches, lozenges, melting tablets and tablets for chewing.

SUMMARY OF THE INVENTION

The present inventors have made the surprising discovery that the stability of nicotine in nicotine delivery products that comprise particles that contain nicotine and cation exchange resin improves with increasing particles size, particularly when included in oral dosage forms such as e.g. chewing gum or lozenges. This effect is clearly documented in both Examples 7 and 8.

Thus, an aspect of the invention pertains to a nicotine delivery product comprising, or even consisting essentially of, a population of nicotine-loaded cation exchange resin particles, said population comprises at least 50% (w/w) particles having a size in the range of 90-300 micron.

Another aspect pertains to a method of producing the nicotine delivery product, the method comprising the steps of:

a) providing a first population of nicotine-loaded cation exchange resin particles, b) optionally reducing the size of one or more of the nicotine-loaded cation exchange resin particles, c) separating a second population of nicotine-loaded cation exchange resin particles from the first population, e.g. by sieving or other suitable particle separation method, said second population comprising at least 50% (w/w) nicotine-loaded cation exchange resin particles having a size in the range of 90-300 micron, thereby providing the nicotine delivery product.

A further aspect of the invention pertains to an alternative method of producing the nicotine delivery product, which method comprises the steps of:

i) providing a population of particulate cation exchange resin material comprising at least 50% (w/w) cation exchange resin particles having a size in the range of 90-300 micron, and ii) loading the cation exchange resin particles with nicotine and optionally also an organic polyol.

An additional aspect of the invention pertains to an oral dosage form comprising a dosage form base and the nicotine delivery product defined herein.

Another aspect of the invention pertains to a method of producing the oral dosage form, the method comprising:

1) providing a nicotine delivery product as defined herein,
2) providing a dosage form base and optionally other ingredients, and
3) combining the nicotine delivery product, the dosage form base and optionally other ingredients so as to prepare the oral dosage form.

Yet an aspect of the invention pertains to the use of a nicotine delivery product as defined herein for increasing the long term stability of nicotine in a nicotine-containing oral dosage form.

DETAILED DESCRIPTION

Figure 1:
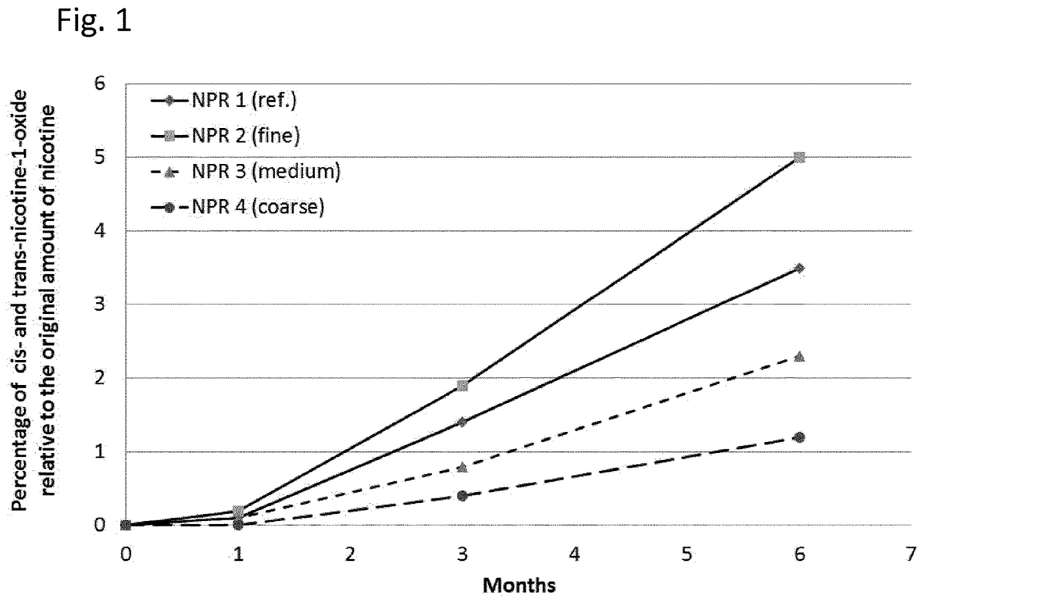
FIG. 1 is a plot of the development of nicotine degradation products, i.e. the sum of cis- and trans-nicotine-1-oxide, in chewing gum samples 1-4 relative to the initial, total amount of nicotine in the samples. The samples packaged in standard blister packaging are stored at accelerated conditions, i.e. 40 degrees C. and 75% RH (relative humidity). Surprisingly, the lowest level of degradation is found in Sample 4 (containing the largest fraction of nicotine-loaded cation exchange resin particles).
Figure 2:
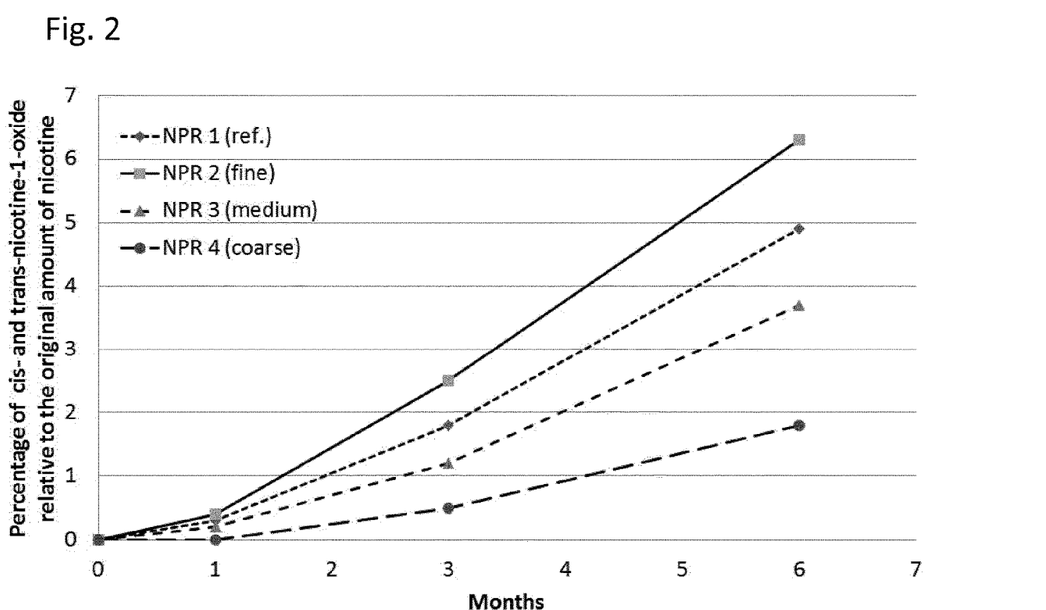
FIG. 2 is a plot of the development of nicotine degradation products, i.e. the sum of cis- and trans-nicotine-1-oxide, in chewing gum samples 5-8 relative to the initial, total amount of nicotine in the samples. The samples packaged in standard blister packaging are stored at accelerated conditions, i.e. 40 degrees C. and 75% RH (relative humidity). Surprisingly, the lowest level of degradation is found in Sample 8 (also containing the largest fraction of nicotine-loaded cation exchange resin particles).

An aspect of the invention pertains to a nicotine delivery product comprising, or even consisting essentially of, a population of nicotine-loaded cation exchange resin particles, said population comprising at least 50% (w/w) particles having a size in the range of 90-300 micron.

In the context of the present invention, the term "nicotine-loaded cation exchange resin particles" pertains to the particles that are obtainable by loading particulate cation exchange resin material with nicotine and comprise both cation exchange resin material and nicotine. A nicotine-loaded cation exchange resin particle may e.g. contain a single piece of cation exchange resin material or multiple pieces of cation exchange resin material that e.g. have aggregated during the production of the nicotine-loaded cation exchange resin particle. Nicotine may both be present in the pores of the resin and/or on the surface of the resin and it may be bound to the functional groups of the resin and/or it may adhere to the resin by other mechanisms.

In the context of the present invention, the terms "population of nicotine-loaded cation exchange resin particles" and "particulate cation exchange resin material", when used to characterise the nicotine delivery product, the oral dosage form, or a method of producing the nicotine delivery product, pertain to the total amount of nicotine-loaded cation exchange resin particles or particulate cation exchange resin material found in the composition in question.

The quantification of the amount of particles having a particle size in a certain size range is performed by sieve analysis as outlined in Example 1, and the term "particle size" therefore relates to the ability of the particles to move through or be retained by sieve holes of a specific size. The amount of particles having a particle size in a certain size range is provided as weight percent relative to the total weight of the particle population in question.

The population of nicotine-loaded cation exchange resin particles may e.g. comprise at least 60% (w/w) particles having a size in the range of 90-300 micron. Preferably, the population comprises at least 70% (w/w) particles having a size in the range of 90-300 micron. Even more preferably, the population comprises at least 80% (w/w) particles having a size in the range of 90-300 micron.

In some preferred embodiments of the invention, the population of nicotine-loaded cation exchange resin particles comprises at least 90% (w/w) particles having a size in the range of 90-300 micron. Preferably, the population comprises at least 95% (w/w) particles having a size in the range of 90-300 micron. Even more preferred, the population comprises at least 99% (w/w) particles having a size in the range of 90-300 micron.

The population of nicotine-loaded cation exchange resin particles may e.g. comprise at least 60% (w/w) particles having a size in the range of 90-250 micron. Preferably, the population comprises at least 70% (w/w) particles having a size in the range of 90-250 micron. Even more preferably, the population comprises at least 80% (w/w) particles having a size in the range of 90-250 micron.

In some preferred embodiments of the invention, the population of nicotine-loaded cation exchange resin particles comprises at least 90% (w/w) particles having a size in the range of 90-250 micron. Preferably, the population comprises at least 95% (w/w) particles having a size in the range of 90-250 micron. Even more preferred, the population comprises at least 99% (w/w) particles having a size in the range of 90-250 micron.

Alternatively, the population of nicotine-loaded cation exchange resin particles may e.g. comprise at least 60% (w/w) particles having a size in the range of 125-300 micron. Preferably, the population comprises at least 70% (w/w) particles having a size in the range of 125-300 micron. Even more preferably, the population comprises at least 80% (w/w) particles having a size in the range of 125-300 micron.

In some preferred embodiments of the invention, the population of nicotine-loaded cation exchange resin particles comprises at least 90% (w/w) particles having a size in the range of 125-300 micron. Preferably, the population comprises at least 95% (w/w) particles having a size in the range of 125-300 micron. Even more preferred, the population comprises at least 99% (w/w) particles having a size in the range of 125-300 micron.

It is also envisioned that the population of nicotine-loaded cation exchange resin particles may e.g. comprise at least 60% (w/w) particles having a size in the range of 200-300 micron. Preferably, the population comprises at least 70% (w/w) particles having a size in the range of 200-300 micron. Even more preferably, the population comprises at least 80% (w/w) particles having a size in the range of 200-300 micron.

In some preferred embodiments of the invention, the population of nicotine-loaded cation exchange resin particles comprises at least 90% (w/w) particles having a size in the range of 200-300 micron. Preferably, the population comprises at least 95% (w/w) particles having a size in the range of 200-300 micron. Even more preferred, the population comprises at least 99% (w/w) particles having a size in the range of 200-300 micron.

It may be preferred that the population of nicotine-loaded cation exchange resin particles comprises at least 60% (w/w) particles having a size in the range of 125-200 micron. Preferably, the population comprises at least 70% (w/w) particles having a size in the range of 125-200 micron. Even more preferably, the population comprises at least 80% (w/w) particles having a size in the range of 125-200 micron.

In some preferred embodiments of the invention, the population of nicotine-loaded cation exchange resin particles comprises at least 90% (w/w) particles having a size in the range of 125-200 micron. Preferably, the population comprises at least 95% (w/w) particles having a size in the range of 125-200 micron. Even more preferred, the population comprises at least 99% (w/w) particles having a size in the range of 125-200 micron.

In several applications it may be preferred that the number of nicotine-loaded cation exchange resin particles that has a particle size larger than 300 micron is kept at a minimum.

Thus, in some preferred embodiments of the invention the population of nicotine-loaded cation exchange resin particles may e.g. comprise at most 5% (w/w) particles having a size larger than 300 micron. Preferably, the population comprises at most 1% (w/w) particles having a size larger than 300 micron. Even more preferably, the population comprises at most 0.1% (w/w) particles having a size larger than 300 micron.

In some preferred embodiments of the invention, the population of nicotine-loaded cation exchange resin particles comprises:
  at least 50% (w/w) particles having a size in the range of 90-300 micron, and
  at most 5% (w/w) particles having a size larger than 300 micron.

In other preferred embodiments of the invention, the population of nicotine-loaded cation exchange resin particles comprises:
  at least 90% (w/w) particles having a size in the range of 90-300 micron, and
  at most 1% (w/w) particles having a size larger than 300 micron.

In further preferred embodiments of the invention, the population of nicotine-loaded cation exchange resin particles comprises:
  at least 50% (w/w) particles having a size in the range of 125-300 micron, and
  at most 5% (w/w) particles having a size larger than 300 micron.

In other preferred embodiments of the invention, the population of nicotine-loaded cation exchange resin particles comprises:
  at least 90% (w/w) particles having a size in the range of 125-300 micron, and
  at most 1% (w/w) particles having a size larger than 300 micron.

The population of nicotine-loaded cation exchange resin particles may e.g. comprise
  at least 90% (w/w) particles having a size in the range of 125-250 micron, and
  at most 1% (w/w) particles having a size larger than 300 micron.

The population of nicotine-loaded cation exchange resin particles may e.g. comprise
  at least 90% (w/w) particles having a size in the range of 125-200 micron, and
  at most 1% (w/w) particles having a size larger than 300 micron.

Alternatively, the population of nicotine-loaded cation exchange resin particles may comprise
  at least 90% (w/w) particles having a size in the range of 200-300 micron, and
  at most 1% (w/w) particles having a size larger than 300 micron.

The present inventors have furthermore observed that the larger nicotine-loaded cation exchange resin particles surprisingly do not appear to provide a significantly delayed release of nicotine from oral dosage forms.

In some embodiments of the invention, the present nicotine delivery system comprising nicotine-loaded cation exchange resin particles even provides a faster release of nicotine from oral dosage forms than similar nicotine delivery systems comprising a larger portion of smaller nicotine-loaded cation exchange resin particles.

The nicotine delivery product preferably has a weight ratio of cation exchange resin to nicotine of about 1:1 to about 10:1. Preferably, the nicotine delivery product has a weight ratio of cation exchange resin to nicotine from 2:1 to 6:1. Most preferred, the nicotine delivery product has a weight ratio of cation exchange resin to nicotine from about 4:1 to about 5:1, preferably about 5:1.

In some preferred embodiments of the invention, the nicotine delivery product is a dry powder and preferably contains only a limited amount of water. In the context of the present invention a dry powder is a powder that has a water content of at most 5% (w/w), which preferably has a dry appearance and is flowable, preferably freely flowable. The determination of whether a powder is free-flowing or not is performed according to US Pharmacopeia 29 NF-24, 1174.

In some preferred embodiments of the invention, the nicotine delivery product has a water content of at most 10% (w/w). Preferably, the nicotine delivery product has a water content of at most 7% (w/w). Even more preferably, the nicotine delivery product has a water content of at most 5% (w/w), such as at most 4% or 3% (w/w).

Alternatively, the nicotine delivery product is a moist powder, a pasta or a slurry.

In some preferred embodiments of the invention, the nicotine delivery product has a water content in the range of 0-50%% (w/w). If the nicotine delivery product is a moist powder, pasta or slurry, it may have a water content in the range of 6-50% (w/w). The nicotine delivery product may e.g. have a water content in the range of 6-15% (w/w). Alternatively, the nicotine delivery product may have a water content in the range of 16-30% (w/w). For example, the nicotine delivery product may have a water content in the range of 31-50% (w/w).

The nicotine delivery product often comprises one or more organic polyols in addition to nicotine and cation exchange resin. The organic polyol typically forms part of the of nicotine-loaded cation exchange resin particles.

Examples of suitable organic polyols are e.g. non-toxic C2 to C12 linear or branched hydrocarbons having at least 2 hydroxy groups and non-toxic C5 to C12 cyclic or heterocyclic hydrocarbons having at least 2 hydroxy groups.

Non-limiting examples of such organic polyols are:
C3:
1,2 Propanediol (propylene glycol), 1,3 propanediol (trimethylene glycol), 1,2,3 propanetriol (glycerol);

C4:
Erythritol;
C5:
Xylitol;
C6:
Sorbitol, mannitol, 1,6 hexanediol, cyclohexanehexyl (inositol);
C12:
Maltitol, maltitol syrup, lactitol, isomalt; and
Mono- and Disaccharides:
Glucose, glucose syrup, fructose, sucrose.

The organic polyol of the nicotine delivery product can be e.g. any of the above polyols or any combination of two or more of the above polyols.

The C3-polyols are presently preferred, and glycerol is particularly preferred.

The nicotine delivery product may for example have a weight ratio between organic polyol and resin in the range 1:0.8 to 1:30, preferably 1:1 to 1:10, most preferably 1:2 to 1:6, such as e.g. about 1:4.

Any pharmaceutical grade cation ion exchange resin useful for binding cationic molecules at the ion exchange sites may be employed in this invention.

Examples of such anionic materials are: those bearing a carboxylic acid group, such as a weakly acidic type of resins containing carboxylic functional groups (these resins are typically derived from polymers or copolymers of methacrylic acid or polymethacrylic acid); the strongly acidic type of resins containing sulfonic functional groups (these resins are typically derived from polymers of styrene or copolymers of styrene and divinylbenzene); or the intermediate acidic type of resins containing phosphonic acid functional groups (these resins are typically derived from polymers of styrene or copolymers of styrene and divinylbenzene).

In some preferred embodiments of the invention, the cation exchange resin comprises one or more resin(s) selected from the group consisting of:
(i) a methacrylic, weakly acidic type of resin containing carboxylic functional groups,
(ii) a copolymer of methacrylic acid and divinylbenzene, said copolymer containing carboxylic functional groups,
(iii) a polystyrene, strongly acidic type of resin containing sulphonic functional groups,
(iv) a polystyrene, intermediate acidic type of resin containing phosphonic functional groups, and
(v) a combination thereof.

In a particularly preferred embodiment of the invention, the cation exchange resin comprises, or even consists essentially of, a copolymer of methacrylic acid and divinylbenzene, said copolymer containing carboxylic functional groups.

The term "consist essentially" means that the relevant embodiment includes the recited element(s) or component(s) but may also contain additional element(s) or component(s) that do not materially affect the basic and novel properties of the invention.

The term "nicotine" pertains both to protonated forms of nicotine, to the free-base form nicotine and to salts thereof.

The amount of nicotine in a composition pertains to the total amount of nicotine if all nicotine is converted to its free-base form. The amount of nicotine is measured using the HPLC method specified in the European Pharmacopeia v. 8.8. Monograph no. 01/2015:1792.

In some preferred embodiments of the invention, the population of nicotine-loaded cation exchange resin particles comprises, or even consists essentially of, Nicotine Polacrilex (also referred to as NPR) CAS No. 96055-45-7.

The nicotine delivery product may furthermore comprise a pH buffer system. Suitable pH buffer systems may for example comprise, or even consist essentially of, sodium carbonate, sodium bicarbonate, potassium carbonate, potassium bicarbonate, potassium citrate and dipotassium phosphate, or mixtures thereof.

As said, it is preferred that the nicotine delivery product comprises, or even consists essentially of, the population of nicotine-loaded cation exchange resin particles.

In some embodiments of the invention, the nicotine delivery product contains at least 50% (w/w) of the population of nicotine-loaded cation exchange resin particles. Preferably, the nicotine delivery product contains at least 70% (w/w) of the population of nicotine-loaded cation exchange resin particles. Even more preferably, the nicotine delivery product contains at least 90% (w/w) of the population of nicotine-loaded cation exchange resin particles, such as e.g. at least 95% of the population of nicotine-loaded cation exchange resin particles. In some preferred embodiments of the invention, the nicotine delivery system consists of the population of nicotine-loaded cation exchange resin particles.

In some preferred embodiments of the invention, the nicotine delivery product
is a particulate product
comprises most 10% (w/w) water,
comprises at least 80% (w/w) of the population of nicotine-loaded cation exchange resin particles, which population of nicotine-loaded cation exchange resin particles comprises
at least 90% (w/w) particles having a size in the range of 90-300 micron, and
at most 1% (w/w) particles having a size larger than 300 micron,
comprises a total amount of organic polyol of at least 1% (w/w), and
comprises a total amount of nicotine of at least 5% (w/w).

In other preferred embodiments of the invention, the nicotine delivery product
is a particulate product
comprises most 5% (w/w) water,
comprises at least 90% (w/w) of the population of nicotine-loaded cation exchange resin particles, which population of nicotine-loaded cation exchange resin particles comprises
at least 90% (w/w) particles having a size in the range of 90-300 micron, and
at most 1% (w/w) particles having a size larger than 300 micron, and
comprises a total amount of organic polyol of at least 5% (w/w), and
comprises a total amount of nicotine of at least 10% (w/w).

In further preferred embodiments of the invention the nicotine delivery product
is a particulate product
comprises most 10% (w/w) water,
comprises at least 80% (w/w) of the population of nicotine-loaded cation exchange resin particles, which population of nicotine-loaded cation exchange resin particles comprises
at least 90% (w/w) particles having a size in the range of 125-300 micron, and
at most 1% (w/w) particles having a size larger than 300 micron, comprises a total amount of organic polyol of at least 1% (w/w), and comprises a total amount of nicotine of at least 5% (w/w).

In yet further preferred embodiments of the invention, the nicotine delivery product
  is a particulate product
  comprises most 5% (w/w) water,
  comprises at least 90% (w/w) of the population of nicotine-loaded cation exchange resin particles, which population of nicotine-loaded cation exchange resin particles comprises
    at least 90% (w/w) particles having a size in the range of 125-300 micron, and
    at most 1% (w/w) particles having a size larger than 300 micron, and
  comprises a total amount of organic polyol of at least 5% (w/w), and
  comprises a total amount of nicotine of at least 10% (w/w).

Yet an aspect of the invention pertains to a method of producing a nicotine delivery product as defined herein, the method comprising the steps of:

a) providing a first population of nicotine-loaded cation exchange resin particles, b) optionally reducing the size of one or more of the nicotine-loaded cation exchange resin particles, c) separating a second population of nicotine-loaded cation exchange resin particles from the first population, e.g. by sieving or other suitable particle separation method, said second population comprising at least 50% (w/w) nicotine-loaded cation exchange resin particles having a size in the range of 90-300 micron, thereby providing the nicotine delivery product.

The first population of nicotine-loaded cation exchange resin particles may be provided in different ways.

The first population of nicotine-loaded cation exchange resin particles may e.g. be a commercially available nicotine/cation exchange resin preparation. For example, the first population of nicotine-loaded cation exchange resin particles may be one or more batches of Nicotine Polacrilex (CAS No. 96055-45-7).

Alternatively, providing the first population of nicotine-loaded cation exchange resin particles may involve providing a population of particulate cation exchange resin material (not loaded with nicotine) and subsequently load the particulate cation exchange resin material with nicotine.

A number of useful processes of loading particulate cation exchange resin material with nicotine have previously been described in the art and any of these may be used.

Non-limiting examples of processes for nicotine-loading of particulate cation exchange resin material can e.g. be found in US 2014/0,230,833 A1, U.S. Pat. Nos. 8,986,668 B2, 8,741,935 B2, 8,728,444 B2, 8,728,443 B2, 6,828,336 B2, 6,586,449 B1 which all are incorporated herein by reference.

The nicotine loading process typically involves the use of water as a processing aid and optionally also organic polyol in addition to nicotine and particulate cation exchange resin material. Excess water is removed from obtained nicotine-loaded cation exchange resin particles, e.g. by drying. The drying step may e.g. involve vacuum drying using a temperature less than 100 degrees C., such as e.g. at most about 80 degrees C., or even more preferred at most about 60 degrees C.

The method may optionally contain a step b) of reducing the particle size of the first population of nicotine-loaded cation exchange resin particles, e.g. by grinding, milling or other suitable technical means for particle size reduction. Step b) is particularly useful if the first population contains a significant amount of particles that are larger than the upper threshold of the desired particle size range (e.g. larger than 300 micron).

Thus, in some preferred embodiments of the invention, the method comprises steps a), b) and c). However, in other preferred embodiments of the invention the method comprises steps a) and c) but not necessarily step b).

In step c) the first population of nicotine-loaded cation exchange resin particles, e.g. obtained from step a) or step b), is separated so as to obtain a fraction that has the desired particle size.

The separation may e.g. involve sieving, dry sedimentation, centrifugation, cyclonic separation, or other useful separation techniques.

A further aspect of the invention pertains to an alternative method of producing a nicotine delivery product as defined herein, the method comprising the steps of:

i) providing a population of particulate cation exchange resin material comprising at least 50% (w/w) particulate cation exchange resin material having a size in the range of 90-300 micron, and ii) loading the cation exchange resin particles with nicotine and optionally also an organic polyol.

In the alternative method the nicotine delivery product is obtained by loading nicotine to a population of particulate cation exchange resin material that already has the desired particle size distribution.

Yet an aspect of the invention pertains to an oral dosage form comprising a dosage form base and a nicotine delivery product as defined herein.

The nicotine delivery product is typically present in dry form when it is present in the final oral dosage form and the individual nicotine-loaded cation exchange resin particles are typically mixed with the dosage form base and distributed uniformly throughout the oral dosage form or at least in a portion of the oral dosage form.

In some preferred embodiments of the invention, the oral dosage form comprises a total amount of the nicotine delivery product in the range of 0.1-100 mg. Preferably, the oral dosage form comprises a total amount of the nicotine delivery product in the range of 1-60 mg. Even more preferably, the oral dosage form comprises a total amount of the nicotine delivery product in the range of 5-50 mg. Most preferably, the oral dosage form comprises a total amount of the nicotine delivery product in the range of 10-30 mg.

The nicotine delivery product is the only nicotine source of the oral dosage form which comprises nicotine loaded on cation exchange resin particles, however, the oral dosage form may contain other nicotine sources such as e.g. free base nicotine or nicotine salts.

In some preferred embodiments of the invention, the oral dosage form comprises a total amount of nicotine in the range of 0.1-10 mg. Preferably, the oral dosage form comprises a total amount of nicotine in the range of 0.5-8 mg. Even more preferably, the oral dosage form comprises a total amount of nicotine in the range of 1-7 mg. Most preferably, the oral dosage form comprises a total amount of nicotine in the range of about 2-about 4 mg.

The weight of the oral dosage form may vary depending on the specific application but in some preferred embodiments of the invention, it is in the range of 0.1-10 g. Preferably, the weight of the oral dosage form is in the range of 0.2-4 g. Even more preferably, the weight of the oral dosage form is in the range of about 1 g-about 2 g.

Alternatively, the weight of the oral dosage form may be in the range of 0.1-1 g, preferably in the range of 0.2-0.4 g.

The oral dosage form, e.g. a chewing gum or a lozenge, may furthermore comprise a pH buffer system.

The pH buffer system assists in the release and conversion of the nicotine salts (ionized nicotine) to nicotine free base (unionized nicotine). Passage of actives across the mucous membranes inside the mouth to the bloodstream and to target tissues is due primarily to passive diffusion of the unionized form of the active. To be effective, the buffer material should be released in sufficient amounts with the release of nicotine to create a basic or alkaline pH environment inside the mouth, thereby facilitating effective delivery to target organs. Consequently, conversion of nicotine in the chewing gum into free base nicotine in mouth saliva is an important step in providing smokers with adequate blood levels of nicotine to reduce craving. Buffer compounds assist with this conversion by raising the pH and thereby facilitating nicotine absorption.

Suitable pH buffer systems may for example comprise, or even consist essentially of, a carbonate salt, a bicarbonate salt, a citrate salt a phosphate salt, a hydrogen phosphate salt, or a combination thereof. Specific examples of useful pH buffers for the pH buffer system are sodium carbonate, sodium bicarbonate, potassium carbonate, potassium bicarbonate, potassium citrate and dipotassium phosphate, or mixtures thereof.

In some preferred embodiments of the invention, it is preferable that the pH buffer system be chosen so as to yield a pH in excess of at least about 7.5 inside the mouth, and even more desirably in excess of about 8.0, or even greater than about 8.5. A pH level of at least about 9.0 is particularly preferred inside the mouth after about 10 minutes, more preferably after about 5 minutes from the onset of mastication. Even more desirable is a pH of at least about 9.0 after about 3 minutes, and especially after about 1 minute. As heretofore stated, the presence of the buffering system not only seems to facilitate absorption of nicotine inside the mouth, but also seems to facilitate the release of nicotine from the nicotine delivery system, in particular nicotine polacrilex, as well as from nicotine salts. At the same time, the buffer system may be preferably optimized in conjunction with the other components so that it does not result in excessive release of nicotine inside the mouth which would overwhelm the user. The quantity and type of buffer materials furthermore should not cause unpleasant organoleptic side effects, such as irritation, burning, coughing or choking, etc.

In some preferred embodiments of the invention, the oral dosage furthermore comprises one or more bulk sweeteners, high intensity sweeteners and/or flavours.

Bulk sweeteners include both sugar and sugarless components. Sugar sweeteners generally include saccharide-containing components commonly known in the chewing gum art, including, but not limited to, sucrose, dextrose, maltose, dextrin, dried invert sugar, fructose, galactose, isomaltulose, corn syrup solids, and the like, alone or in combination.

Sorbitol can be used as a sugarless sweetener. Additionally, sugarless sweeteners can include, but are not limited to, other sugar alcohols such as mannitol, hydrogenated isomaltulose (isomalt), xylitol, hydrogenated starch hydrolysates, maltitol, erythritol, lactitol and the like, alone or in combination.

Examples of useful high intensity sweeteners are sucralose, aspartame, salts of acesulfame, alitame, saccharin and its salts, cyclamic acid and its salts, glycyrrhizin, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in the oral dosage form.

The oral dosage form is preferably selected from the group consisting of a chewing gum, a lozenge, a chewable tablet, an orally disintegrating tablet, a hard boiled dosage form, and an orodispersible film.

In some preferred embodiments of the invention, the oral dosage form is a chewing gum comprising a gum base.

In general, a chewing gum composition typically comprises a water-soluble bulk portion, a water-insoluble chewable gum base portion and flavoring agents. The water-soluble portion dissipates with a portion of the flavoring agent over a period of time during chewing. The gum base portion is retained in the mouth throughout the chew.

The gum base is the masticatory substance of the chewing gum, which imparts the chew characteristics to the final product. The gum base typically defines the release profile of flavors and sweeteners.

The insoluble portion of the gum typically may contain any combination of elastomers, vinyl polymers, elastomer plasticizers, waxes, softeners, fillers and other optional ingredients such as colorants and anti-oxidants.

The composition of gum base formulations can vary substantially depending on the particular product to be prepared and on the desired masticatory and other sensory characteristics of the final product. However, typical ranges (% by weight of the gum base) of the above gum base components are: 1 to 40% elastomeric compounds, 5 to 55% elastomer plasticizers, 0 to 40% waxes, 5 to 35% softeners, 0 to 50% fillers, and 0 to 5% miscellaneous ingredients such as antioxidants, colorants, etc.

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

The elastomer may be any water-insoluble elastomeric polymer known in the art, and includes those gum polymers utilized for chewing gum and bubble gum listed in Food and Drug Administration, CFR, Title 21, Section 172,615, as "Masticatory Substances of Natural Vegetable Origin" and "Masticatory Substances, Synthetic". Useful natural elastomers include natural rubber such as smoked or liquid latex and guayule, natural gums such as jelutong, lechi caspi, perillo, sorva, massaranduba balata, massaranduba chocolate, nispero, rosidinha, chicle, gutta percha, gutta kataiu, niger gutta, tunu, chilte, chiquibul, gutta hang kang.

Useful synthetic elastomers include high-molecular weight elastomers such as butadiene-styrene copolymers and isobutylene-isoprene copolymers, low-molecular weight elastomers such as polybutene, polybutadiene and polyisobutylene, vinyl polymeric elastomers such as polyvinyl acetate, polyethylene, vinyl copolymeric elastomers such as vinyl acetate/vinyl laurate, vinyl acetate/vinyl stearate, ethylene/vinyl acetate, polyvinyl alcohol or mixtures thereof.

It is e.g. common in the industry to combine in a gum base a synthetic elastomer having a high-molecular weight and a low-molecular-weight elastomer. Presently, preferred combinations of synthetic elastomers include, but are not limited to, polyisobutylene and styrene-butadiene, polyisobutylene and polyisoprene, polyisobutylene and isobutylene-isoprene copolymer (butyl rubber) and a combination of polyisobutylene, styrene-butadiene copolymer and isobutylene isoprene copolymer, and all of the above individual synthetic polymers in admixture with polyvinyl acetate, vinyl acetate-vinyl laurate copolymers, respectively and mixtures thereof.

The gum base may optionally also comprise, or even essentially consist of, biodegradable polymers rendering the gum base and chewing gum formulation biodegradable. Such polymers include, but are not limited to polyesters, prolamine, zein, corn gluten, wheat gluten, gliadin, glutenin and any combinations thereof.

Polyester may e.g. include polyester obtained through polymerization of cyclic esters and polyester obtained through a condensation process of di- or polyfunctional acids and di- or polyfunctional alcohols. Variations of such polymers may include polyesters obtained through other suitable types and modifications of polymerization processes. Particularly useful polyesters include polylactic acid and polylactide.

If non-tack chewing gum is desired, copolymers of methyl vinyl ether and maleic acid and derivatives thereof, such as Gantrez, and/or copolymers of polyisoprene-graft maleic anhydride (PIP-g-MA) with polyethylene-glycol (PEG) or methoxy-polyethylene-glycol (MPEG) side chains, such as REV-7 provided by Revolymer, may be among the gum base polymers.

Elastomer plasticizers vary the firmness of the gum base. Their specificity on elastomer inter-molecular chain breaking (plasticizing) along with their varying softening points cause varying degrees of finished gum firmness and compatibility when used in base. This may be important when one wants to provide more elastomeric chain exposure to the alkanoic chains of the waxes.

Elastomer plasticizers suitable for use in the present invention include natural rosin esters often referred to as ester gums or natural resins. Such elastomer plasticizers known in the art are methyl, glycerol and pentaerythritol esters of rosins and modified rosins, such as hydrogenated, dimerized and polymerized rosins. Examples are glycerol ester of wood and gum rosin, glycerol ester of partially hydrogenated wood and gum rosin, glycerol ester of polymerized wood and gum rosin, glycerol ester of partially dimerized wood and gum rosin, glycerol ester of tall oil rosin, pentaerythritol ester of wood and gum rosin, pentaerythritol esters of partially and fully hydrogenated wood and gum rosin, methyl esters of wood and gum rosins and partially and fully hydrogenated methyl esters of wood and gum rosin.

The synthetic elastomer plasticizers, which are also referred to as synthetic resins, include low molecular weight polyvinyl acetate (i.e. molecular weight below about 25,000 g/mol) and terpene resins derived from alpha-pinene, beta-pinene and/or d-limonene.

The selection of softeners has an influence on the softness of the base. Softeners modify the texture, cause the hydrophobic and hydrophilic components of the base to be miscible, and may further plasticize the synthetic elastomers of the gum base. The emulsifiers which belong to the group of softeners provide the gum base with water-binding properties which confer to the gum base a pleasant smooth surface and reduce its adhesive properties.

Softeners suitable for use in the gum base include one or more waxes. The one or more waxes may for example be selected from the group consisting of paraffin waxes, microcrystalline waxes, polyethylene waxes, natural waxes and combinations thereof. The softener may alternatively or additionally contain tri-glycerides such as e.g. triglycerides of non-hydrogenated, partially hydrogenated and fully hydrogenated vegetable oils and tallow, cocoa butter and degreased cocoa powder and a combination thereof.

Alternatively or additionally, the softener may contain one or more emulsifiers. Useful examples of emulsifiers include monoglycerides, diglycerides, acetylated mono and diglycerides, distilled mono- and diglycerides, glycerol monostearate, propylene glycol monostearate, Na-, K-, Mg- and Ca-stearates, glycerol triacetate, fatty acid monoglycerides (e.g. stearic, palmitic, oleic and linoleic acids), lactic acid esters and acetic acid esters of mono- and diglycerides, sugar esters of edible fatty acids also referred to as sucrose polyesters including those disclosed in WO 00/25598, lecithin and hydroxylated lecithin. Often the emulsifier contains a triglyceride level of less than 5% by weight.

Fillers used in gum base modify the texture of the gum base and aid in processing. The particle size of the filler has an effect on cohesiveness, density and processing characteristics of the gum base and its compounding. The smaller the particle size, the more dense and cohesive the final gum base. Also, by selecting fillers based on their particle size distribution, initial mass compounding may be varied, thus allowing alteration of the compounding characteristics of the initial mass during gum base processing and ultimately the final chew characteristics of gums made from these gum bases.

Fillers suitable for use in the gum base include magnesium carbonate, calcium carbonate, ground limestone, and silicate types such as magnesium and aluminum silicate, kaolin, and clay, aluminum oxide, silicium oxide, talc, as well as titanium oxide, mono-, di- and tricalcium phosphate, sodium sulphate, cellulose polymers or mixtures thereof.

Antioxidants prolong shelf life and storage of gum base, finished gum or their respective components including fats and flavor oils. Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof.

Flavorants and colorants impart characteristics or remove or mask undesired characteristics. Colorants may typically include FD&C type lakes, plant extracts, fruit and vegetable extracts and titanium dioxide flavorants may typically include cocoa powder, heat-modified amino acids and other vegetable extracts.

Gum bases are typically prepared by adding an amount of the elastomer, elastomer plasticizer and filler, and on occasion a vinyl polymer, to a heated (100 degrees C.-120 degrees C.) sigma blade mixer with a front to rear speed ratio of from about 1.2:1 to about 2:1, the higher ratio typically being used for gum base which requires more rigorous compounding of its elastomers.

The initial amounts of ingredients comprising the initial mass may be determined by the working capacity of the mixer in order to attain a proper consistency and by the degree of compounding desired to break down the elastomer and increase chain branching. The higher the level of filler at the start or selection of a filler having a certain particle size distribution, the higher the degree of compounding and shearing of the elastomer, thus lower viscosity gum bases and thus softer final gum base and gum made from such a gum base. The longer the time of compounding, the use of lower molecular weight or softening point gum base ingredients, the lower the viscosity and firmness of the final gum base.

Compounding typically begins to be effective once the ingredients have massed together. Anywhere from 15 minutes to 90 minutes may be the length of compounding time.

Preferably, the time of compounding is from 20 minutes to about 60 minutes. The amount of added elastomer plasticizer depends on the level of elastomer and filler present. If too much elastomer plasticizer is added, the initial mass becomes over plasticized and not homogeneous.

After the initial ingredients have massed homogeneously and been compounded for the time desired, the balance of the gum base ingredients are added in a sequential manner until a completely homogeneous molten mass is attained. Typically, any remainder of elastomer, elastomer plasticizer, vinyl polymer and filler, are added within 60 minutes after the initial compounding time. The filler and the elastomer plasticizer would typically be individually weighed and added in portions during this time. The optional waxes and the softeners are typically added after the elastomer and elastomer plasticizers and during the next 60 minutes. Then the mass is allowed to become homogeneous before dumping.

Typical gum base processing times may vary from about one to about three hours, preferably from about 1½ to 2½ hours, depending on the formulation. The final mass temperature when dumped may be between 70 degrees C. and 130 degrees C. and preferably between 100 degrees C. and 120 degrees C. The completed molten mass is emptied from the mixer into coated or lined pans, extruded or cast into any desirable shape and allowed to cool and solidify.

Those skilled in the art will recognize that many variations of the above-described procedure may be followed.

The water-soluble portion of the chewing gum may comprise chewing gum ingredients such as softeners, sweeteners, high-intensity sweeteners, flavoring agents, acidulants, fillers, anti-oxidants, and other components that provide desired attributes.

Gum base typically comprises about 20% to about 90%, preferably from about 40% to about 70% by weight of the chewing gum. Softeners typically comprise from about 0.5% to about 25% by weight of the chewing gum. The bulking agents generally comprise from about 5% to about 90%, preferably from about 20% to about 80% by weight of the chewing gum. High-intensity sweeteners in gum typically may range from about 0.01 to 1.0 weight percent. Flavoring agents may be present in the chewing gum in amount within the range of from about 0.1 to about 30 weight percent of the chewing gum.

The chewing gum (uncoated) may e.g. comprise:
20-80% (w/w) gum base,
5-30% (w/w) filler,
0.2-5% of the nicotine delivery product,
1-10% pH buffer system,
5-50% bulk sweetener,
0-1% high intensity sweetener, and
0.1-5% flavour.

The chewing gum may e.g. be a conventional chewing gum in which water-soluble ingredients are kneaded with gum base to form a dough-like chewing gum mass which is shaped into individual chewing gum pieces using e.g. extrusion, rolling and/or scoring equipment well known to those skilled in the art.

In other preferred embodiments of the invention, the chewing gum is a compressed chewing gum comprising at least one compressed module. Useful examples of compressed chewing gum are e.g. found in US 2008/0286340 A1, WO 2004068965, WO 2009/143,841 A1, and WO 2009/080,022A1 which all are incorporated herein by reference.

The nicotine delivery product may e.g. be blended with the gum base, e.g. by kneading, and is preferably distributed uniformly in the gum base along with the other chewing gum ingredients. Alternatively or additionally, if the oral dosage form is a compressed chewing gum at least some of the nicotine delivery product may be compressed together with particles containing gum base.

In some preferred embodiments of the invention, the oral dosage form is a lozenge.

Lozenges are solid preparations that are intended to dissolve or disintegrate slowly in the mouth. They typically contain one or more medicaments, usually in a flavoured, sweetened base. They can e.g. be prepared by molding (e.g. using a gelantine and/or fused sucrose or sorbitol base) or by compression of sugar- or polyol-based tablets.

Useful examples of lozenges are e.g. found in WO2009/134,947 A1 which is incorporated herein by reference.

In some preferred embodiments of the invention, the lozenge comprises lozenge base and the nicotine delivery product of the present invention.

The lozenge base suitable for compressed lozenges typically contains:
a bulking agent,
a pH buffering system,
a dissolution modifier,
an anti-sticking agent, and
optionally flavours and/or sweeteners.

In some preferred embodiments of the invention, the lozenge therefore comprises
the nicotine delivery product as defined herein,
a bulking agent,
a pH buffering system as defined herein,
a dissolution modifier,
an anti-sticking agent, and
optionally flavours and/or sweeteners.

The lozenge may e.g. comprise:
0.1-5% (w/w) of the nicotine delivery product as defined herein,
50-90% (w/w) bulking agent,
0.5-10% (w/w) pH buffering system as defined herein,
2-15% (w/w) dissolution modifier,
0.1-5% anti-sticking agent, and
0.1-5% flavours and/or high intensity sweeteners.

Suitable bulk agents include, but are not limited to, maltitol, maltose, fructose, glucose, trehalose, sorbitol, sucrose, mannitol, xylitol, isomalt, dextrose, maltodextrin, dextrates, dextrin, erythritol, lactitol, polydextrose and mixtures thereof. In some embodiments, the filler is mannitol. In some embodiments, the mannitol is present from about 100 mg to about 300 mg per lozenge, in another embodiment from about 150 mg to about 200 mg per lozenge.

Dissolution modifiers suitable for use in the present invention include, but are not limited to, acacia, agar, alginic acid or a salt thereof, carbomer, carboxymethylcellulose, carrageenan, cellulose, chitosan, copovidone, cyclodextrins, ethylcellulose, gelatin, guar gum, hydroxyethyl cellulose, hydroxyethyl methylcellulose, hydroxypropyl cellulose, hypromellose, inulin, methylcellulose, pectin, polycarbophil or a salt thereof, polyethylene glycol, polyethylene oxide, polyvinyl alcohol, pullulan, starch, tragacanth, trehalose, xanthan gum and mixtures thereof. In some embodiments, the dissolution modifiers included within the formulations of the present invention are selected from the group consisting of alginic acid or a salt thereof, polycarbophil or a salt thereof, xanthan gum and mixtures thereof.

Additional optional excipients may also be included in the formulations of the present invention, such as processing and stabilizing aids. Processing and stabilizing aids include, but are not limited to, chelating agents, anti-oxidants or preservatives, anti-sticking agents, or colorants. Antioxidants/preservatives suitable for use in the present invention may include sodium benzoate, butyl-hydroxy toluene and tocopherol and its salts. Anti-sticking agents suitable for use herein include, but are not limited to, talc, corn starch, stearic acid, calcium stearate, polyethylene glycol, colloidal silicon dioxide, sodium stearyl fumarate, magnesium stearate, vegetable and mineral oils and mixtures thereof. In some embodiments the anti-sticking agent is magnesium stearate.

Suitable colorants for use herein include any pigments, dyes, lakes or natural food colors that are suitable for food and drug applications, e.g. FD&C dyes and lakes.

Dosage forms such as chewable tablet, an orally disintegrating tablet, a hard boiled dosage form, and an orodispersible film are well-known in the art.

Useful but non-limiting examples of chewable tablets, orally disintegrating tablets, hard boiled candy dosage form, and orodispersible films are e.g. found in US 20080286340 A1 which is incorporated herein by reference.

In some preferred embodiments of the invention, the oral dosage form, e.g. a chewing gum or a lozenge, has a coating. The oral dosage form may e.g. be a coated chewing gum.

Yet an aspect of the invention pertains to a method of producing an oral dosage form as defined herein, the method comprising:
1) providing a nicotine delivery product as defined herein,
2) providing a dosage form base and optionally other ingredients
3) combining the nicotine delivery product, the dosage form base and optionally other ingredients so as to prepare the oral dosage form.

In some preferred embodiments of the invention, the method is a method of producing a chewing gum or a lozenge.

Additional details regarding the producing of chewing gum or lozenges can be found above.

A further embodiment of the invention pertains to the use of a nicotine delivery product as defined herein for increasing the long term stability of nicotine in a nicotine-containing oral dosage form. The nicotine delivery product is used as an ingredient in the production of the oral dosage form and e.g. as primary, and optionally, even the only source of nicotine of the oral dosage form.

The increase of the long term stability of nicotine mentioned above is preferably due to reduced oxidative degradation of nicotine in the oral dosage form during storage. Oxidative degradation may e.g. involve degradation of nicotine to cis- and trans-nicotine-1-oxide. The increase in long term stability is preferably obtained without additional delay of the release of nicotine from the dosage form during the administration of the dosage forms.

Another aspect of the invention pertains to the nicotine delivery product defined herein for use as a medicament.

Yet an aspect of the invention pertains to the oral dosage form defined herein for use as a medicament.

A further aspect of the invention pertains to the nicotine delivery product defined herein for use in nicotine replacement therapy and/or for treatment or prevention of smoking withdrawal syndrome.

An additional aspect of the invention pertains to the oral dosage form defined herein for use in nicotine replacement therapy and/or for treatment or prevention of smoking withdrawal syndrome.

EXAMPLES

The following Examples illustrate the method of the present invention and the nicotine delivery product resulting from such method. These Examples should not be regarded as limiting the invention in any sense.

Example 1

Determination of Particle Size Distribution by Sieve Analysis

This example describes how to determine the particle size distribution of a nicotine-loaded cation exchange resin particles or a particulate cation exchange resin material by means of sieve analysis.

Materials:

Sieving tower (Vibratory Sieve Shaker AS 200 control, Retch Gmbh, Germany)

90 micron sieve, 125 micron sieve, 200 micron sieve, 250 micron sieve, and 300 micron sieve Procedure:

a) A representative sample of the nicotine delivery product to be tested is taken and the water content of the nicotine delivery product is adjusted to 2% (w/w) if necessary.

b) Approx. 60 g of the sample (the precise weight is recorded) having a water content of 5% is subjected to sieving analysis using the sieving tower. The sieving tower is set to operate with a vertical amplitude of 1.5 mm and a frequency of 50 Hz until the separation is complete (typically approx. 15 minutes).

c) The weight of the sample fraction in each sieve is measured and the weight percentages of the corresponding particle size fractions are calculated.

Example 2

Preparation of Nicotine Polacrilex (NPR) Samples with Different Particle Size Distributions (PSD)

500 g of a standard batch of NPR (CAS 96055-45-7) with a load of approximately 15% nicotine "Nicotine Polacrilex, 15%, USP" obtained from Cambrex Corporation, USA was selected for testing.

Approximately 415 g of the NPR sample having a water content of 2.0% was fractionated by sieving using the Retsch sieving device of Example 1 with a set of sieves having the following pores size: 250 micron, 200 micron, 125 micron, and 90 micron and at an amplitude of 1.5 mm for 15 minutes to obtain three particle size fractions (NPR 2, NPR3, and NPR 4) in addition to the original NPR sample (NPR 1). The particle size distributions of the four NPR samples are shown below:

TABLE 1

Particle size distribution of four samples of nicotine polacrilex (NPR 1, NPR 2, NPR 3 and NPR 4).

| Particle size (μm) | Particles size distribution (% wt.) | | | |
|---|---|---|---|---|
| | NPR 1 (original sample) | NPR 2 (fine particles) | NPR 3 (medium particles) | NPR 4 (coarse particles) |
| 0-90 | 53.2 | 100.0 | 0.0 | 0.0 |
| 90-125 | 39.2 | 0.0 | 100.0 | 0.0 |
| 125-200 | 6.9 | 0.0 | 0.0 | 90.8 |
| 200-250 | 0.7 | 0.0 | 0.0 | 9.2 |
| >250 | 0.0 | 0.0 | 0.0 | 0.0 |

Example 3

Preparation of Gum Base

A gum base was prepared using the ingredients of Table 2.

TABLE 2

Ingredients of the gum base used for chewing gum preparation.

| Ingredients | % by weight |
|---|---|
| Elastomer | 10 |
| Natural resin | 28 |
| Synthetic resin | 22 |
| Fat/wax/emulsifiers | 23 |
| Fillers | 17 |

The elastomer and filler were added to a mixer provided with mixing means, e.g. horizontally placed Z-shaped arms. The mixer had been preheated for 15 minutes to a temperature of about 120° C. The rubber was sheared and grinded with mechanical action in the mixer.

Resin was slowly added to the elastomer and filler until the mixture became homogeneous. The remaining resin was then added to the kettle and mixed for 10-20 minutes. The softening ingredients were added and mixed for 20-40 minutes until the whole mixture became homogeneous.

The mixture was then discharged into the pan and allowed to cool to room temperature from the discharged temperature of about 120° C.

Example 4

Preparation of Nicotine-Containing Chewing Gum

Chewing gum was prepared by use of the NPR samples in Example 2 and the gum base in Example 3. The chewing gum was prepared according to a conventional mechanical mixing procedure as described in Table 3.

TABLE 3

Ingredients of the chewing gums CG1-CG8.

| Ingredients | CG1 | CG2 | CG3 | CG4 | CG5 | CG6 | CG7 | CG8 |
|---|---|---|---|---|---|---|---|---|
| Gum base (Example 3) | 57.4% | 57.4% | 57.4% | 57.4% | 54% | 54% | 54% | 54% |
| Calcium carbonate Filler | 14.6% | 14.6% | 14.6% | 14.6% | 12% | 12% | 12% | 12% |
| Nicotine Polacrilex (from Example 2): | | | | | | | | |
| NPR 1 | 1.3% | | | | 1.3% | | | |
| NPR 2 | | 1.3% | | | | 1.3% | | |
| NPR 3 | | | 1.3% | | | | 1.3% | |
| NPR 4 | | | | 1.3% | | | | 1.3% |
| Sodium hydrogen carbonate | 1.0% | 1.0% | 1.0% | 1.0% | 1.0% | 1.0% | 1.0% | 1.0% |
| Sodium carbonate | 2.0% | 2.0% | 2.0% | 2.0% | 2.0% | 2.0% | 2.0% | 2.0% |
| Sorbitol bulk sweetener | 21.4% | 21.4% | 21.4% | 21.4% | 26.3% | 26.3% | 26.3% | 26.3% |
| High Intensity Sweetener | 0.3% | 0.3% | 0.3% | 0.3% | 0.4% | 0.4% | 0.4% | 0.4% |
| Flavor | 2.0% | 2.0% | 2.0% | 2.0% | 3.0% | 3.0% | 3.0% | 3.0% |

Gum base and filler were mixed batch-wise in a mixer provided with mixing means, e.g. horizontally placed Z-shaped arms. The mixer had been preheated to a temperature of up to approximately 50°C.

When the content was homogenous, the other ingredients were added according to a specified time schedule. Nicotine formulated as NPR was added in the first half of the mixing process.

Finally, after mixing, chewing gum pieces were formed through extrusion, rolling and scoring. Each piece of chewing gum comprised 2 mg of nicotine.

Alternatively, the mixing step may be performed continuously in a conventional extruder process, partly or fully replacing the mixing involving the Z-blade mixer.

The chewing gum samples provide two series of chewing gums (CG1-CG4 and CG5-CG8) in which the composition is fixed in each series except for the particle size distribution of the NPR used.

Example 5

Preparation of Nicotine-Containing Lozenge

Nicotine containing lozenges were prepared by blending of the NPR samples obtained from Example 2 with other excipients followed by direct compression to yield the compositions described in Table 4.

TABLE 4

Composition of four different lozenge samples (LOZ1-LOZ4).

| Ingredients | LOZ1 mg | LOZ2 mg | LOZ3 mg | LOZ4 mg |
|---|---|---|---|---|
| Mannitol | 1025.34 | 1025.34 | 1025.34 | 1025.34 |
| Potassium bicarbonate | 2.8 | 2.8 | 2.8 | 2.8 |
| Sodium carbonate | 22.75 | 22.75 | 22.75 | 22.75 |
| Sodium alginate | 63.70 | 63.70 | 63.70 | 63.70 |
| Calcium polycarbophil | 31.73 | 31.73 | 31.73 | 31.73 |
| Xanthan gum | 12.25 | 12.25 | 12.25 | 12.25 |
| Nicotine Polacrilex (ex 1) | | | | |
| NPR 1 | 22.22 | | | |
| NPR 2 | | 22.22 | | |
| NPR 3 | | | 22.22 | |
| NPR 4 | | | | 22.22 |
| Magnesium stearate | 12.00 | 12.00 | 12.00 | 12.00 |
| High Intensity Sweetener | 6.00 | 6.00 | 6.00 | 6.00 |
| Flavor | 1.20 | 1.20 | 1.20 | 1.20 |
| Lozenge total | 1200.00 | 1200.00 | 1200.00 | 1200.00 |

The lozenges were prepared by mixing the ingredients listed in the table and compressing the combined powder mixture to obtain lozenges of total weight 1200 mg.

Example 6

Evaluation of Nicotine Release of CG1-CG8

The release of nicotine from the chewing gum samples of Example 4 was determined in vitro. The measurements were carried out according to the procedure set forth in the Ph. Eur. $6^{th}$ ed. 2.9.25, in a phosphate buffer with pH=7.4, a chewing rate of 60 chew per minute, and with the temperature of the medium set at 37° C.

A piece of chewing gum was chewed for specified time intervals of 0, 5, 10, 20 and 30 minutes. Then, the nicotine content of the gum before and after chewing was analyzed according to standard HPLC-techniques. For each chewing gum sample, the analysis was repeated 6 times, and the average result was reported as the percentage of nicotine released compared to the nicotine content of the sample before chewing (see Table 5).

TABLE 5

Results from the in vitro release experiments.

| | In vitro release, % | | | |
|---|---|---|---|---|
| | 5 min | 10 min | 20 min | 30 min |
| CG1 | 11 | 35 | 62 | 76 |
| CG2 | 13 | 34 | 61 | 75 |
| CG3 | 10 | 34 | 62 | 76 |
| CG4 | 10 | 38 | 66 | 79 |
| CG5 | 10 | 32 | 59 | 75 |
| CG6 | 12 | 33 | 61 | 75 |
| CG7 | 9 | 35 | 61 | 75 |
| CG8 | 9 | 32 | 63 | 76 |

The variation in nicotine release at each time point and between comparable sample sets (i.e. CG1-CG4 and CG5-CG8 respectively) is observed to be very limited, and it is within the uncertainty of the analysis method applied.

Hence, it is concluded that variation in the NPR particle size does not systematically influence the nicotine release from the chewing gum.

Example 7

Evaluation of Nicotine Stability of CG1-CG8—Accelerated Conditions

The chewing gum samples of Example 4 were packed in standard blister packages and stored in a climate chamber at controlled conditions 40° C./75% RH (relative humidity).

Then, at pre-defined time points blisters from each sample were taken out of the climate chamber and analyzed by HPLC for nicotine degradation products. Nicotine primarily degrades to cis- and trans-nicotine-1-oxide, and the degradation profiles (reported as a percentage denoting the sum of cis- and trans-nicotine-1-oxide relative to the initial content of nicotine) described in Table 6 were found:

TABLE 6

Nicotine degradation profiles for 8 chewing gum samples stored at accelerated conditions. Results below the analysis quantification limit (ie. no detectable degradation) are denoted BPQL.

| | | Sum of cis- and trans-nicotine-1-oxide, % of initial content of nicotine | | | |
|---|---|---|---|---|---|
| CG no. | NPR sample | 0 mths | 1 mth | 3 mths | 6 mths |
| CG1 | NPR 1 (ref) | BPQL | 0.1 | 1.4 | 3.5 |
| CG2 | NPR 2 (fine) | BPQL | 0.2 | 1.9 | 5.0 |
| CG3 | NPR 3 (medium) | BPQL | 0.1 | 0.8 | 2.3 |
| CG4 | NPR 4 (coarse) | BPQL | BPQL | 0.4 | 1.2 |
| CG5 | NPR 1 (ref) | BPQL | 0.3 | 1.8 | 4.9 |
| CG6 | NPR 2 (fine) | BPQL | 0.4 | 2.5 | 6.3 |
| CG7 | NPR 3 (medium) | BPQL | 0.2 | 1.2 | 3.7 |
| CG8 | NPR 4 (coarse) | BPQL | BPQL | 0.5 | 1.8 |

Surprisingly, the results within each series of chewing gum with identical formulations except for the NPR show that the coarser the NPR particles, the less pronounced the nicotine degradation is—compare CG2-CG4 and CG6-CG8, respectively.

The results for the reference samples CG1 and CG5 containing un-sieved NPR are consistent with the observed effect of NPR particle size on nicotine degradation as the un-sieved NPR primarily comprise particles of size 0-90 μm but also some coarser particles.

Example 8

Evaluation of Nicotine Stability of CG5-CG8—Real Time Conditions

The chewing gum samples CG5-CG8 of Example 4 were packed in standard blister packages and stored in a climate chamber at controlled conditions 25° C./60% RH (relative humidity).

Then, at pre-defined time points blisters from each sample were taken out of the climate chamber and analyzed by HPLC for nicotine degradation products. Nicotine primarily degrades to cis- and trans-nicotine-1-oxide, and the degradation profiles (reported as a percentage denoting the sum of cis- and trans-nicotine-1-oxide relative to the initial content of nicotine) described in Table 6 were found.

TABLE 7

Nicotine degradation profiles for 4 chewing gum samples stored at accelerated conditions. Results below the analysis quantification limit (ie. no detectable degradation) are denoted BPQL.

| | | Sum of cis- and trans-nicotine-1-oxide, % of initial content of nicotine | | |
|---|---|---|---|---|
| CG no. | NPR sample | 0 mths | 6 mth | 12 mths |
| CG5 | NPR 1 (ref) | BPQL | BPQL | 0.2 |
| CG6 | NPR 2 (fine) | BPQL | 0.1 | 0.4 |
| CG7 | NPR 3 (medium) | BPQL | BPQL | 0.1 |
| CG8 | NPR 4 (coarse) | BPQL | BPQL | BPQL |

Surprisingly, but consistent with Example 7, the results demonstrate that coarser NPR particles provide less the nicotine degradation (e.g. seen by comparing the amounts of degradation products for CG6-CG8 after 12 months).

This discovery opens up for new types of nicotine delivery products wherein the particle size distribution of the nicotine-loaded cation exchange resin particles is designed to provide the optimum stability of the product.

The invention claimed is:

1. A nicotine delivery product consisting of a population of particles, said particles consisting of nicotine-loaded cation exchange resin or a combination of nicotine-loaded cation exchange resin and one or more organic polyols,
   wherein the cation exchange resin consists of a copolymer of methacrylic acid and divinylbenzene, said copolymer containing carboxylic functional groups, and
   wherein at least 90% (w/w) of said particles has a size in the range of 90-300 micron.

2. The nicotine delivery product according to claim 1, wherein at least 10% (w/w) of said particles has a size in the range of 125-300 micron.

3. The nicotine delivery product according to claim 1, wherein at least 90% (w/w) of said particles has a size in the range of 125-300 micron.

4. The nicotine delivery product according to claim 1, having a weight ratio of cation exchange resin to nicotine of about 1:1 to about 10:1.

5. The nicotine delivery product according to claim 1, having a water content of at most 10% (w/w).

6. The nicotine delivery product according to claim 1, wherein said particles consist of a combination of nicotine-loaded cation exchange resin and one or more organic polyols.

7. The nicotine delivery product according to claim 6, wherein the one or more organic polyols is glycerol or a combination of glycerol and one or more other organic polyols.

8. The nicotine delivery product according to claim 6, wherein said particles has a weight ratio between organic polyol and resin in the range of 1:0.8 to 1:30.

9. The nicotine delivery product according to claim 1, wherein the nicotine delivery product is a dry powder.

10. An oral dosage form comprising a dosage form base and a nicotine delivery product according to claim 1.

11. The oral dosage form according to claim 10, the oral dosage form comprising a total amount of the nicotine delivery product in the range of 0.1-100 mg.

12. The oral dosage form according to claim 10, the oral dosage form comprising a total amount of nicotine in the range of 0.1-10 mg.

13. The oral dosage form according to claim 10, the oral dosage form having a weight in the range of 0.1-10 g.

14. The oral dosage form according to claim 10, wherein the oral dosage form is selected from the group consisting of a chewing gum, a lozenge, a chewable tablet, an orally disintegrating tablet, a hard boiled dosage form, and an orodispersible film.

15. The oral dosage form according to claim 10, wherein the oral dosage form is a chewing gum comprising a gum base.

16. The oral dosage form according to claim 15, wherein the chewing gum is a compressed chewing gum comprising at least one compressed module.

17. The oral dosage form according to claim 15, wherein the nicotine delivery product is blended with the gum base.

18. The oral dosage form according to claim 16, wherein the nicotine delivery product is compressed together with particles containing gum base.

19. The oral dosage form according to claim 15, wherein the chewing gum has a coating.

20. The oral dosage form according to claim 10, wherein the oral dosage form is a lozenge.

21. The nicotine delivery product according to claim 1, wherein the particles of nicotine-loaded cation exchange resin are particles of nicotine polacrilex.

22. A nicotine delivery product consisting of a population of particles consisting of nicotine polacrilex resin and one or more organic polyols, wherein at least 90% (w/w) of said particles has a size in the range of 90-300 micron.

* * * * *